United States Patent
Lattuada et al.

(10) Patent No.: US 12,129,563 B2
(45) Date of Patent: Oct. 29, 2024

(54) ELECTROCHEMICAL IODINATION OF N,N'-(2,3-DIHYDROXYPROPYL)-5-HYDROXY-1,3-BENZENEDICARBOXAMIDE

(71) Applicant: BRACCO IMAGING S.P.A., Milan (IT)

(72) Inventors: Luciano Lattuada, Cassina de' Pecchi (IT); Camilla Cavallotti, Novara (IT); Giovanni Battista Giovenzana, Novara (IT); Fulvio Uggeri, Codogno (IT); Alessandro Minguzzi, Milan (IT); Alberto Vertova, Treviglio (IT); Letizia Sorti, Dalmine (IT); Carlo Morelli, Cambiago (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 18/694,306

(22) PCT Filed: Sep. 22, 2022

(86) PCT No.: PCT/EP2022/076320
§ 371 (c)(1),
(2) Date: Mar. 21, 2024

(87) PCT Pub. No.: WO2023/046815
PCT Pub. Date: Mar. 30, 2023

(65) Prior Publication Data
US 2024/0271295 A1    Aug. 15, 2024

(30) Foreign Application Priority Data

Sep. 24, 2021  (EP) .................................... 21198848
Jul. 13, 2022  (EP) .................................... 22184631

(51) Int. Cl.
C25B 3/27          (2021.01)
C07C 231/12     (2006.01)
(Continued)

(52) U.S. Cl.
CPC ............... *C25B 3/27* (2021.01); *C07C 231/12* (2013.01); *C07C 237/46* (2013.01); *C25B 3/07* (2021.01);
(Continued)

(58) Field of Classification Search
CPC .......... C25B 3/11; C25B 3/27; C07C 231/12; C07C 231/46; C07C 23/12; C07C 237/46
(Continued)

(56) References Cited

FOREIGN PATENT DOCUMENTS

EP    2093206 A1 *  8/2009  ............. C07B 39/00
WO   0032561 A1    6/2000
(Continued)

OTHER PUBLICATIONS

Gallotti et al., "The chemistry of iomeprol and physico-chemical properties of its aqueous solutions and pharmaceutical formulations," Eur. J. Radiol., 18(S1), S1-S12 (1994).
(Continued)

Primary Examiner — Edna Wong
(74) Attorney, Agent, or Firm — VIVICAR Law, PLLC (57) ABSTRACT

The invention is related to a process for preparing a iodinating X-rays contrast agent. More specifically, it relates to a process for the preparation of N,N'-bis-(2,3-dihydroxypropyl)-5-hydroxy-2,4,6-triiodo-1,3-benzenedicarboxaniide (I) by electrochemical iodination of N,N'-(2,3-dihydroxypropyl)-5-hydroxy-1,3-benzenedicarboxamide (II) with molecular iodine (I2) which is in situ electrochemically generated from a source of iodide ions (I−). The iodide ions (I−) are obtained by the dissolution of hydrogen iodide (HI) or an alkali metal iodide in the reaction medium or produced
(Continued)

during the reaction of N,N'-(2,3-dihydroxypropyl)-5-hydroxy-1,3-benzenedicarboxamide with I2. The invention also relates to the use of the intermediate compound of formula (I), obtained through the above electrochemical iodination of compound (II), in the preparation of N,N'-bis[2,3-dihydroxypropyl]-5(hydroxyacetyl)methylamino]-2,4,6-triiodo-1,3-benzenedicarboxamide (iomeprol).

15 Claims, 4 Drawing Sheets

(51) Int. Cl.
  *C07C 237/46* (2006.01)
  *C25B 3/07* (2021.01)
  *C25B 3/09* (2021.01)
  *C25B 3/11* (2021.01)
  *C25B 15/08* (2006.01)

(52) U.S. Cl.
  CPC .................. *C25B 3/09* (2021.01); *C25B 3/11* (2021.01); *C25B 15/081* (2021.01); *C25B 15/083* (2021.01); *C25B 15/087* (2021.01)

(58) Field of Classification Search
  USPC .......................... 205/359, 459; 570/127, 190
  See application file for complete search history.

(56) References Cited

FOREIGN PATENT DOCUMENTS

| WO | 2009103666 A2 | 8/2009 |
| WO | 2011003894 A1 | 1/2011 |
| WO | 2011154500 A1 | 12/2011 |

OTHER PUBLICATIONS

International Search Report and Written Opinion for PCT/EP2022/076320, mailed Dec. 14, 2022.

* cited by examiner

ELECTROCHEMICAL IODINATION OF N,N'-(2,3-DIHYDROXYPROPYL)-5-HYDROXY-1,3-BENZENEDICARBOXAMIDE

CROSS-REFERENCE TO RELATED APPLICATIONS

This application is the national stage application of corresponding international application number PCT/EP2022/076320, filed Sep. 22, 2022, which claims priority to and the benefit of European application no. 21198848.0, filed Sep. 24, 2021, and European application no. 22184631.4, filed Jul. 13, 2022, which are hereby incorporated by reference in their entireties.

The present invention refers to a process for the preparation of a iodinating X-rays contrast agent. More specifically, it relates to a process for the preparation of N,N'-(2,3-dihydroxypropyl)-5-hydroxy-2,4,6-triiodo-1,3-benzenedicarboxamide (I) by electrochemical iodination of N,N'-(2,3-dihydroxypropyl)-5-hydroxy-1,3-benzenedicarboxamide (II), and to the use of the product thus obtained as an intermediate in the synthesis of Iomeprol.

BACKGROUND OF THE INVENTION

Contrast agents and their use in the diagnostic field are widely described in literature. In particular, iodinated aromatic derivatives are among the classes of compounds that find an application as contrast agent in diagnostic techniques which rely on the absorption of X-rays by the tissues or organs (e.g. radiography, tomography). Among these aromatic iodinated derivatives, it is worth to mention, inter alia, Iomeprol (N, N'-bis[2,3-dihydroxypropyl]-5(hydroxyacetyl) methylamino]-2,4,6-triiodo-1,3-benzenedicarboxamide), a radiographic contrast agent well known and widely used in daily diagnostic practice (A. Gallotti et al., *Eur. J. Radiol.* 1994, 18(S1), S1-S12).

Like most of the iodinated X-ray contrast agents, the chemical structure of Iomeprol comprises a tri-iodinated aromatic nucleus, which provides the enhanced contrast effect, and is typically obtained from a derivative of the 5-hydroxy-1,3-benzenedicarboxylic acid which undergoes tri-iodination in positions 2, 4 and 6 of the aromatic ring. For a general reference to the synthetic route in the industrial preparation of Iomeprol see for instance WO00/32561.

The tri-iodination reaction on the aromatic nucleus may be carried out according to different procedures known in the art. In the industrial process currently used for preparing Iomeprol, or other iodinated X-ray contrast agents, the iodination of the aromatic substrate is typically carried out using solutions of iodine monochloride (ICl) in concentrated hydrochloric acid (HCl).

However, this method suffers from several drawbacks, mainly related to the extremely acidic working conditions, which become increasingly harsh due to the hydrochloric acid produced during the reaction, to the toxicity and the corrosivity of the iodinating agent employed and to its limited storage lifetime.

Iodine monochloride (ICl) is prepared for instance by reaction of elemental iodine with chlorine, which is an extremely poisonous gas, involving the need of strict precautions and safety arrangements because of its toxicity and hazard. Iodine monochloride (ICl) reacts with pure water to give HCl, iodine and oxygen and for this reason stable aqueous solutions of ICl can only be obtained in presence of large amounts of chloride anions (e.g. NaCl, KCl or HCl).

Alternatively, as described in WO2011/003894, 3 moles of ICl can be prepared by reacting with molecular iodine ($I_2$) a iodine derivative having oxidation state of iodine equal to (III) which is obtained by electrochemically oxidating 1 mole of starting ICl. The iodinating species however needs to be then transferred into a different compartment to perform the iodination reaction, with problems of difficult handling and possible low stability of the solutions.

In any case, the iodination of N,N'-(2,3-dihydroxypropyl)-5-hydroxy-1,3-benzenedicarboxamide with ICl must be performed at controlled pH and temperature (25° C.) to achieve good yields and purity. This implies that large amounts of a base (e.g. NaOH) must be added to the reaction medium not only to neutralize the acidity generated by the reaction but also to neutralize the hydrochloric acid in which the ICl is dissolved. Since this neutralization reaction is extremely exothermic, the base must be slowly added, in order to keep the temperature below 25° C. and avoid the formation of by-products; as a result, longer reaction times are needed.

As an alternative to the use of ICl, the iodination reaction may be also performed with molecular iodine ($I_2$) in an aqueous medium, but the drawback of this approach is that half of the added iodine is lost in the form of iodide ions during the reaction, especially providing hydroiodic acid (HI). Moreover, the iodination of an aqueous solution of N,N'-(2,3-dihydroxypropyl)-5-hydroxy-1,3-benzenedicarboxamide with molecular iodine alone gives only poor yields of the corresponding tri-iodinated compound, always as a mixture with by-products such as the mono-iodinated and di-iodinated intermediates, since during the reaction part of the molecular iodine combines with the iodide ions in solution forming unreactive poly-iodide ions, such as for instance tri-iodide ions ($I_3^-$).

In order to exploit all the iodine used for the reaction and to overcome the above issues, an oxidizing agent, such as iodic acid ($HIO_3$), is usually added to the mixture (see for instance WO 2011/154500).

As a further alternative, a process has been described in WO2009/103666 wherein the iodination of 3,4-disubstituted phenols is achieved by means of electrochemically generated iodine cations ($I^+$). According to this disclosure, a $I^+$ solution is obtained before the iodination in a separate compartment by inserting a platinum sheet anode in a stock solution of iodine in a solvent, such as methanol, and performing the electrolysis in galvanostatic mode. A substrate to be iodinated is then added portionwise to the so obtained $I^+$ solution and iodination is done by refluxing to achieve the conversion.

The above method suffers from some drawbacks, for instance because the solution of iodinating agent ($I^+$) must be transferred to a separate compartment to perform the iodination and, as a consequence, the yield of the process can be affected by the limited stability and storage life of $I^+$.

Iodine is a very expensive reagent, thus for an efficient and economic process it would be desirable to exploit any amount used thereof for the iodination reaction, for instance by recovering and recycling it, for minimizing any possible loss.

Furthermore, with the above-mentioned synthetic approach, it is necessary to add a further step for the removal of the solvent by evaporation.

To overcome the above issues, it has now been found that N,N'-(2,3-dihydroxypropyl)-5-hydroxy-2,4,6-triiodo-1,3-benzenedicarboxamide can be efficiently prepared by using molecular iodine ($I_2$) as iodinating specie which is in situ electrochemically regenerated once reacted or generated by reduction of iodide ions present in the reaction medium.

Advantageously, the synthesis of the invention achieves conversion yields of 90% or higher with minimal loss of iodine.

SUMMARY OF THE INVENTION

The invention relates to a process for preparing N,N'-bis-(2,3-dihydroxypropyl)-5-hydroxy-2,4,6-triiodo-1,3-benzenedicarboxamide by reacting the intermediate N,N'-(2,3-dihydroxypropyl)-5-hydroxy-1,3-benzenedicarboxamide with molecular iodine ($I_2$) which is in situ electrochemically generated from a source of iodide ions ($I^+$). Such iodide ions can derive from the dissolution of HI or an alkali metal iodide (e.g. NaI, KI) in the reaction medium or may be obtained directly from the reaction of N,N'-(2,3-dihydroxypropyl)-5-hydroxy-1,3-benzenedicarboxamide with molecular iodine ($I_2$).

DETAILED DESCRIPTION OF THE INVENTION

It is a first aspect of the present invention a process for the preparation of N,N'-bis-(2,3-dihydroxypropyl)-5-hydroxy-2,4,6-triiodo-1,3-benzenedicarboxamide (I), comprising the steps of a) dissolving N,N'-(2,3-dihydroxypropyl)-5-hydroxy-1,3-benzenedicarboxamide (II) in a reaction medium in the presence of molecular iodine ($I_2$) and b) iodinating said compound (II) with molecular iodine ($I_2$) to obtain said compound (I), wherein the reaction medium is an aqueous solution and the molecular iodine ($I_2$) is in situ electrochemically generated from a source of iodide ions ($I^-$).

Preferably the aqueous solution is water.

The electrochemical step b) of the invention can be performed in galvanostatic or potentiostatic mode.

According to a preferred embodiment, the iodide ions ($I^-$) are provided by the addition and dissolution of hydrogen iodide (HI) or an alkali metal iodide into the reaction medium or produced during the reaction of $I_2$ with the compound of formula (II) according to step b).

The step b) of the process can also be represented by the following Scheme 1

The reaction is an electrophilic substitution wherein one atom of iodine ($I_2$) substitutes a hydrogen atom in the aromatic ring while the second atom of iodine is released as iodide ($I^-$).

Because of the stoichiometry of the iodination reaction of the present invention, at least three moles of the reactive specie $I_2$ are required for each mole of the aromatic substrate of formula (II) to be tri-iodinated to the corresponding compound of formula (I).

Preferably, the molar ratio of molecular iodine ($I_2$) to N,N'-(2,3-dihydroxypropyl)-5-hydroxy-1,3-benzenedicarboxamide (II) may vary in the range from 3:1 to 1.5:1, preferably from 2:1 to 1.5:1.

In some preferred embodiments, the steps a) and b) of the process are both carried out in the same single compartment of an undivided electrolytic cell comprising two electrodes selected from those conventionally adopted in industrial applications both an anode and a cathode.

Preferably, said electrolytic cell comprising the aqueous solution of N,N'-(2,3-dihydroxypropyl)-5-hydroxy-1,3-benzenedicarboxamide (II) is equipped with a carbon based cathode (e.g. made of graphite) and a anode made of a metal selected from those typically used in similar electrochemical system (e.g. platinum or other elements of the Group VIIIB of the periodic table). Such metals can be for instance in the form of a grid, a foil or in a reticular form. The anode can also be made by materials suitably coated with a sufficiently thick film of the above metals.

Alternatively, for pulsating or alternating current experiments it is possible to use a cathode made of platinum or of other layers typically adopted in anodes for industrial electrochemistry, such as $Ta_2O_2$, $IrO_2$, $RuO_2$ or $SnO_2$.

Conveniently, in such embodiments the electrolytic generation of $I_2$ according to the present invention may be performed in galvanostatic mode, i.e. by operating with application of a constant current density during the process, while the aqueous solution is magnetically stirred. Preferably, a constant current is passed through the solution during the process, comprised in the range from 5 to 100 mA/cm². More preferably, the constant current is comprised in the range from 5 to 20 mA/cm².

Alternatively in another preferred embodiment, the steps a) and b) of the process can be carried out in a two compartments electrolytic cell. One advantage of using this type of cells is that of limiting the risk of de-iodination of the final product (I) at the cathode once it has reached its maximum concentration.

The compartments can be divided by a permeable separator, such as for instance a porous barrier or diaphragm or a permeable membrane, such as an ionic exchange membrane.

In one embodiment, the presence of a porous septum provides a poor separation between the compartments, which allows to keep the pH constant while still enabling the diffusion and/or migration of both OH⁻ and H⁺/Na⁺ ions.

Figure 3:
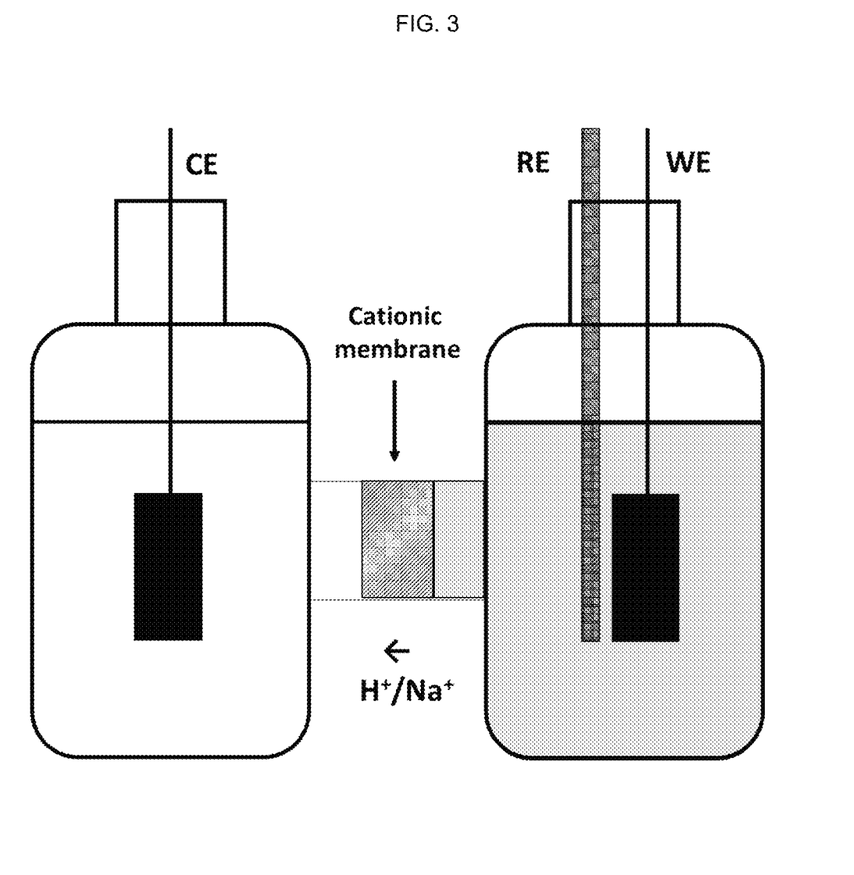
FIG. 3 represents a two-compartments electrochemical cell used according to another preferred embodiment of the invention for preparing N,N'-(2,3-dihydroxypropyl)-5-hydroxy-2,4,6-triiodo-1,3-benzenedicarboxamide (I) by reacting N,N'-(2,3-dihydroxypropyl)-5-hydroxy-1,3-benzenedicarboxamide (II) with molecular iodine ($I_2$) which is electrochemically regenerated in situ from iodide ions ($I^-$) obtained by the reaction of compound (II) with $I_2$. The two compartments are separated by a cationic membrane (one compartment equipped with a working electrode WE and a reference electrode RE and the other equipped with a counter electrode CE) and the electrolysis is carried out in potentiostatic mode.

Alternatively, a membrane guarantees a stronger separation. Examples of suitable membranes are represented by anionic membranes, which allow an automatic flux of OH⁻ ions from the cathode to the anode balancing the pH decrease at the latter, or cationic membranes, which can be crossed by H⁺ and Na⁺ fluxing from the anode to the cathode (see one example of such configuration in FIG. 3). More conveniently, a cationic membrane is used for the process of the invention, in particular in case of industrial scale up.

Preferred anionic membranes are made of a polymeric core such as polyamide, polyester, polystyrene, polyvinyl benzene and the like.

Preferred cationic membranes are polymeric fluorocarbonic membranes, selected for instance from the group consisting of polytetrafluoroethylene (PTFE), tetrafluoroethylene-perfluoropropylene copolymers (FEP), tetrafluoroethylene-perfluoroalkoxy copolymers (PFA), ethylene-tetrafluoroethylene copolymers (ETFE), polyvinylidene fluoride (PVDF) membranes and derivatives thereof. More preferably the cationic membrane is tetrafluoroethylene-perfluoro-3,6-dioxa-4-methyl-7-octenesulfonic acid copolymer (Nafion® 117).

Suitable anodes in this case may comprise graphitic or vitreous carbon anodes. Preferably, the anode can be made of graphite, carbon paper or carbon cloth, the latter optionally in combination with carbon felt.

As the cathode, the conventional metals can be employed. Preferably, the cathode can be made of platinum, nickel, inox steel and the like and can be electron-conducting materials having different structures, such as for instance a full solid-state material or a material forming a three-dimensional network of electron-conducting pathways.

Preferably the two compartments cell is a filter-press cell, which can be also suitable for a flow electrolysis reaction on industrial scale.

In a first embodiment of the invention, molecular iodine ($I_2$) is electrochemically generated from an external source of iodide ions (I⁻) added to the reaction medium. According to this embodiment, the process comprises the steps of:

a') dissolving N,N'-(2,3-dihydroxypropyl)-5-hydroxy-1,3-benzenedicarboxamide (II) in a reaction medium to which a source of iodide ions (I⁻) has been added and b') iodinating said compound (II) with molecular iodine ($I_2$) to obtain said compound (I), wherein the reaction medium is an aqueous solution and the molecular iodine ($I_2$) is in situ electrochemically generated from the added source of iodide ions (I⁻).

Preferably the aqueous solution is water.

Preferably, the electrochemical reaction according to this embodiment is carried out in galvanostatic mode.

The source of iodide ions (I⁻) can be obtained through the dissolution of hydrogen iodide (HI) or of an alkali metal iodide added to the reaction medium.

Typically, the alkali metal iodide is selected from sodium iodide (NaI), potassium iodide (KI), lithium iodide (LiI) and caesium iodide (CsI), preferably it selected from NaI and KI.

Hydroiodic acid (HI) or a suitable metal iodide (e.g. NaI or KI) is dissolved in the reaction medium in a molar ratio of iodide (I⁻) to N,N'-(2,3-dihydroxypropyl)-5-hydroxy-1,3-benzenedicarboxamide (II) ranging from 6:1 to 3:1, preferably from 4:1 to 3:1. Normally, the iodide is used in a slight excess.

Preferably, the solution is maintained at a constant temperature ranging from 20° C. to 75° C., more preferably from 50° C. to 60° C., during the iodination reaction of step b') by operating according to conventional methods. Even more preferably, the reaction of step b') is carried out at the temperature of 50° C.

The reaction medium is maintained at a pH neutral, i.e. comprised in the range from 5 to 7.5, preferably between 6 and 7, by continuous addition of a protic acid, such as for instance $H_2SO_4$.

According to the invention, the iodide ions (I⁻) are oxidized onto the anode surface to molecular iodine ($I_2$) based on the following reaction:

$$2I^- \rightarrow I_2 + 2e^-$$

In step b') the molecular iodine so generated reacts with N,N'-(2,3-dihydroxypropyl)-5-hydroxy-1,3-benzenedicarboxamide (II) in solution. This reaction is an electrophilic substitution in which one atom of molecular iodine ($I_2$) substitutes a hydrogen atom in the aromatic ring of N,N'-(2,3-dihydroxypropyl)-5-hydroxy-1,3-benzenedicarboxamide (II) while the second atom of iodine is released as iodide ion (I⁻).

The released iodide ion (I⁻) is in situ recycled by being electrochemically re-oxidized to molecular iodine ($I_2$). In this way, all the iodine atoms put in the cell compartment are completely exploited for the iodination reaction. Protons (H⁺) are also generated in this process and they are reduced to gaseous hydrogen ($H_2$) onto the cathode surface.

Figure 1:
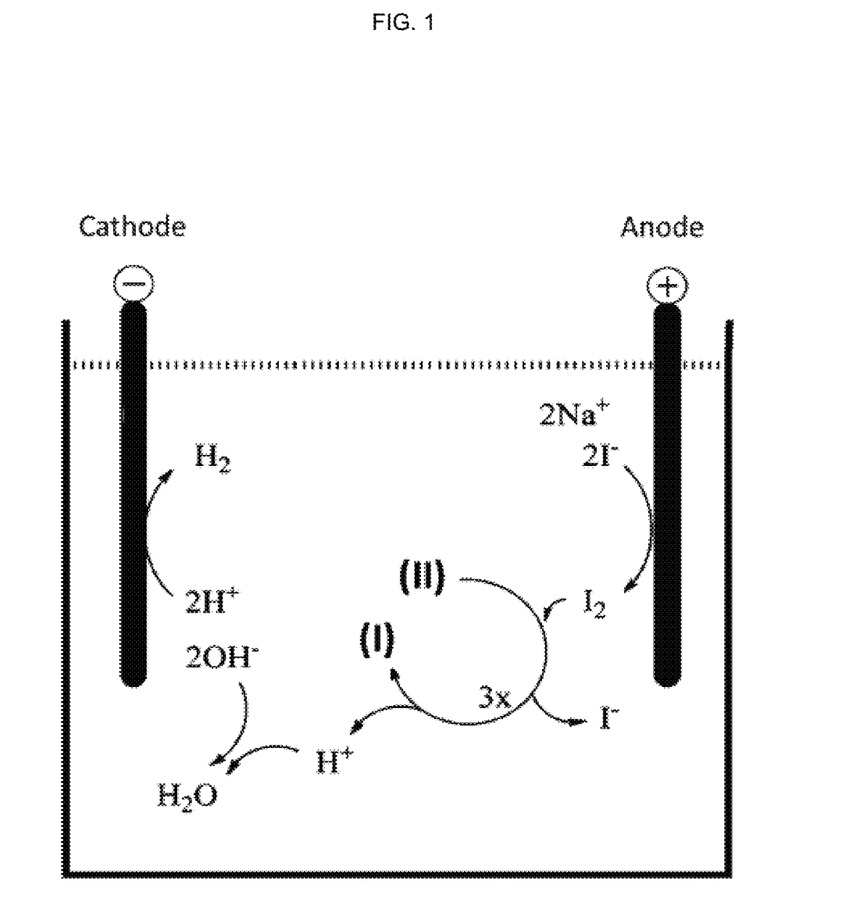
FIG. 1 represents a scheme of the reaction according to one embodiment of the invention for preparing N,N'-(2,3-dihydroxypropyl)-5-hydroxy-2,4,6-triiodo-1,3-benzenedicarboxamide (I) by reacting N,N'-(2,3-dihydroxypropyl)-5-hydroxy-1,3-benzenedicarboxamide (II) with molecular iodine ($I_2$) which is electrochemically generated in situ from iodide ions ($I^-$) obtained by the dissolution of sodium iodide (NaI) in water. The electrochemical cell is an undivided cell equipped with a cathode in graphite and an anode in platinum (25×25 mm) and the electrochemical reaction is carried out under galvanostatic control.

The reactions involved in the process are schematically reported in FIG. 1, wherein the alkali metal iodine NaI is used. The stoichiometry of the reactions involved in this process are reported below:

Cathodic reaction: $6H_2O+6e^- \rightarrow 3H_2+6OH^-$

Anodic reaction: $6NaI \rightarrow 3I_2+6e^-+6Na^+$

Compound (II)iodination: $3I_2+$Compound (II)$\rightarrow$Compound (1)$+3H^++3I^-$ Overall reaction: $3NaI+3H_2O+$Compound (II)$\rightarrow$Compound (1)$+3NaOH+3H_2$ The reaction time depends on the reaction conditions, mainly depending on the combination of the current density applied and the electrode surface employed, but also on the ratio between the reactants; purity; temperature, etc. The person of ordinary skill in the art can find the optimal conditions by recurring to his personal knowledge and experience. The completion of the reaction can be detected by ordinary analytical means used in organic chemistry, like spectrometric equipment, for example HPLC.

Typically, the reaction is completed in a time ranging from 3 hours to 48 hours, generally from 6 hours to 12 hours.

As the generation of $I_2$ generally occurs at a rate higher than its consumption rate in the reaction with N,N'-(2,3-dihydroxypropyl)-5-hydroxy-1,3-benzenedicarboxamide (II), the electrochemically generated $I_2$ tends to settle onto the anode, which becomes violet, and slowly dissolves by reaction with N,N'-(2,3-dihydroxypropyl)-5-hydroxy-1,3-benzenedicarboxamide (II). In order to allow the complete dissolution of the iodine deposited onto the anode, the constant electric current can be periodically switched off.

In a preferred embodiment, the current is conveniently switched off for intervals from 30 to 60 seconds every 2-5 minutes.

As a further option, a pulsating current can be applied between the electrodes to achieve the same result.

In a second embodiment of the invention, $I_2$ is in situ electrochemically re-generated from iodide ions ($I^-$) produced by the reaction of N,N'-(2,3-dihydroxypropyl)-5-hydroxy-1,3-benzenedicarboxamide (II) with molecular iodine ($I_2$) by applying a constant current.

According to this embodiment, the process comprises the steps of:

a") dissolving N,N'-(2,3-dihydroxypropyl)-5-hydroxy-1,3-benzenedicarboxamide (II) in a reaction medium in the presence of molecular iodine ($I_2$);

b"$_1$) partially iodinating said compound (II) with molecular iodine ($I_2$) in the absence of any electric current, and b"$_2$) applying an electric current to the reaction obtained in step b"$_1$) to complete the iodination and obtain said compound (I), wherein the reaction medium is an aqueous solution and the molecular iodine ($I_2$) is in situ electrochemically re-generated in step b"$_2$) from the iodide ions ($I^-$) produced during the reaction of step b"$_1$).

Preferably the aqueous solution is water.

Preferably, the electrochemical reaction according to this embodiment is carried out in galvanostatic mode.

In one embodiment, an aqueous solution of N,N'-(2,3-dihydroxypropyl)-5-hydroxy-1,3-benzenedicarboxamide (II) is placed into an undivided electrochemical cell equipped with a graphite cathode and a platinum anode.

Step a") is carried out by adjusting the pH of the aqueous solution after the dissolution of compound (II) to a value >6, preferably >10, with a base such as NaOH or KOH, or alternatively by using a preformed solution of N,N'-(2,3-dihydroxypropyl)-5-hydroxy-1,3-benzenedicarboxamide (II) in water having pH>6, preferably >10.

Step b"$_1$) is carried out without application of electric current. In this way, a partial iodination of N,N'-(2,3-dihydroxypropyl)-5-hydroxy-1,3-benzenedicarboxamide (II) is achieved. Compound (I) is obtained along with the corresponding mono- and di-iodinated intermediates and iodide ions ($I^-$) are released from the reaction. Preferably, the molar ratio of $I_2$ to N,N'-(2,3-dihydroxypropyl)-5-hydroxy-1,3-benzenedicarboxamide (II) is in the range from 3:1 to 1.5:1, preferably from 2:1 to 1.5:1.

The reaction is preferably carried out at a temperature ranging from 40° C. to 60° C., more conveniently of about 55° C., and for a time ranging from 1 hour to 6 hours, typically from 2 hours to 3 hours.

Step b"$_2$) is carried out by applying electric current, preferably a constant current (galvanostatic mode), to the magnetically stirred solution obtained from step b"$_1$). In this way, the iodide ions obtained in step b"$_1$) after the iodination reaction are re-oxidized to molecular iodine ($I_2$) which reacts with the remaining N,N'-(2,3-dihydroxypropyl)-5-hydroxy-1,3-benzenedicarboxamide (II) or with the corresponding mono and di-iodinated intermediates present in the reaction mixture.

The solution is maintained at a temperature ranging from 40° C. to 60° C., preferably 55° C. For instance, the applied electric current can be comprised in the range from 5 to 100 mA/cm$^2$. Typically, a constant electric current of 5-20 mA/cm$^2$ is applied for a time ranging from 3 hours to 48 hours, generally for 6-12 hours.

The reaction medium is maintained at a pH neutral, i.e. comprised in the range from 5 to 7.5, preferably between 6 and 7, by continuous addition of a protic acid, such as for instance $H_2SO_4$.

As the regeneration of $I_2$ generally occurs at a rate higher than its consumption rate in the reaction with N,N'-(2,3-dihydroxypropyl)-5-hydroxy-1,3-benzenedicarboxamide (II), the regenerated $I_2$ tends to settle onto the anode, which becomes violet, and slowly dissolves by reaction with N,N'-(2,3-dihydroxypropyl)-5-hydroxy-1,3-benzenedicarboxamide (II). In order to allow the complete dissolution of the iodine deposited onto the anode the constant electric current can be periodically switched off. In a preferred embodiment, the current is conveniently switched off for an interval from 30 to 60 seconds every 2-5 min.

As a further option, a pulsating current can be applied between the electrodes to achieve the same result.

As a further option, an alternating current can be applied between the electrodes to achieve the same result.

Figure 2:
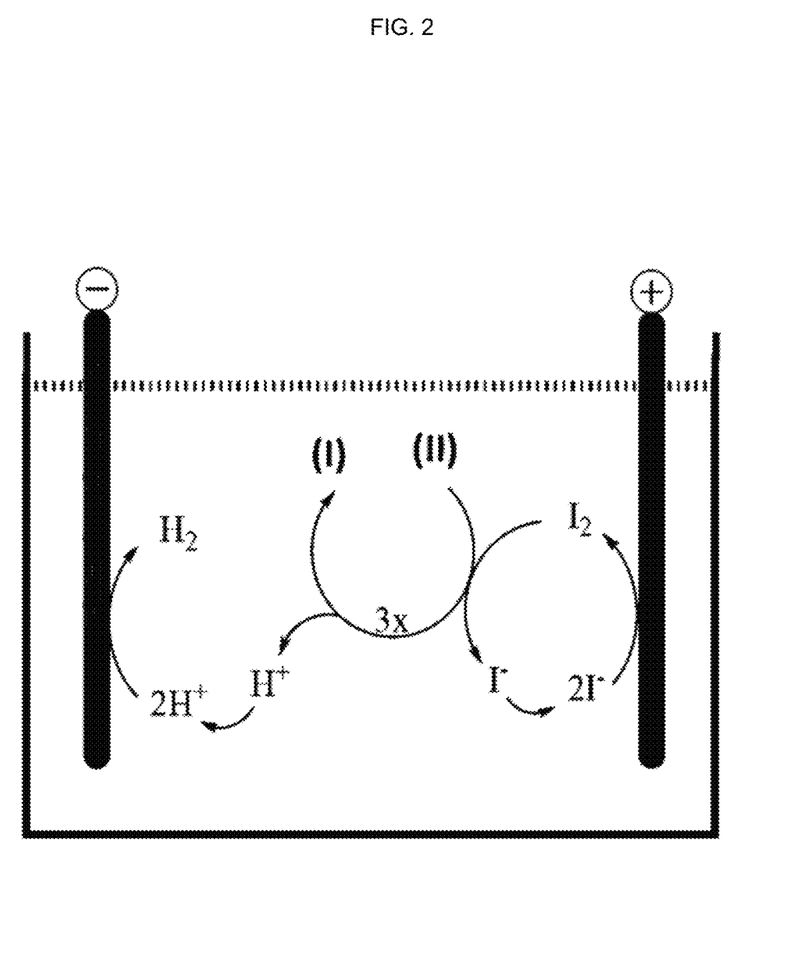
FIG. 2 represents a scheme of the reaction according to another embodiment of the invention for preparing N,N'-(2,3-dihydroxypropyl)-5-hydroxy-2,4,6-triiodo-1,3-benzenedicarboxamide (I) by reacting N,N'-(2,3-dihydroxypropyl)-5-hydroxy-1,3-benzenedicarboxamide (II) with molecular iodine ($I_2$) which is electrochemically regenerated in situ from iodide ions ($I^-$) obtained by the reaction of compound (II) with $I_2$. The electrochemical cell is an undivided cell equipped with a cathode in graphite and an anode in platinum (25×25 mm) and the electrochemical reaction is carried out under galvanostatic control.

The reactions involved in this second embodiment of the process are schematically reported in FIG. 2. The stoichiometry of the reactions involved in this process are reported below:

Compound (I)iodination: $6I_2+2$Compound (II)$\rightarrow 2$Compound (I)$+6H^++6I^-$ Cathodic process: $6H^++6e^- \rightarrow 3H_2$ Anodic reaction: $6I^- \rightarrow 3I_2+6e^-$ Overall reaction: $3I_2+2$Compound (II)$\rightarrow 2$Compound (I)$+3H_2$ The reaction of iodination of N,N'-(2,3-dihydroxypropyl)-5-hydroxy-1,3-benzenedicarboxamide (II) produces three iodide ions and three protons for each product molecule.

The iodide ions would be lost during the work-up of the reaction, generating a loss of 50% of the precious halogen atoms.

Advantageously, the electrochemical reaction of step b"$_2$) allows to re-oxidize the produced iodide ions and to reintroduce them into the process until they are completely used and/or until the compound (II) is completely converted to compound (I).

In a third embodiment of the invention, $I_2$ is in situ electrochemically re-generated from iodide ions (I$^-$) produced by the reaction of N,N'-(2,3-dihydroxypropyl)-5-hydroxy-1,3-benzenedicarboxamide (II) with molecular iodine ($I_2$) by applying a constant voltage across the electrodes so as to have an anode potential from 0.5 V to 0.9 V versus SCE (Saturated Calomel Electrode as reference electrode).

According to this embodiment, the process comprises the steps of:
- a") dissolving N,N'-(2,3-dihydroxypropyl)-5-hydroxy-1,3-benzenedicarboxamide (II) in a reaction medium in the presence of molecular iodine ($I_2$);
- b"$_1$) partially iodinating said compound (II) with molecular iodine ($I_2$) in the absence of any voltage, and
- b"$_2$) applying a voltage to the reaction obtained in step b"$_1$) to complete the iodination and obtain said compound (I), wherein the reaction medium is an aqueous solution and the molecular iodine ($I_2$) is in situ electrochemically re-generated in step b"$_2$) from the iodide ions (I$^-$) produced during the reaction of step b"$_1$).

The electrochemical reaction according to this embodiment is carried out in potentiostatic mode.

Preferably the aqueous solution is an electrolyte such as aqueous NaOH. More preferably it is a NaOH solution with a concentration ranging from 0.1 M to 0.5 M.

Preferably, the aqueous solution of N,N'-(2,3-dihydroxypropyl)-5-hydroxy-1,3-benzenedicarboxamide (II) is placed into a two compartments electrochemical cell equipped with a carbon based anode and a cathode made of platinum or stainless steel.

Step a") is carried out by adjusting the pH of the aqueous solution after the dissolution of compound (II) to a value comprised between 8 and 12 with a base such as NaOH of KOH.

Step b"$_1$) is a chemical phase, carried out without application of any voltage. In this way, a partial iodination of N,N'-(2,3-dihydroxypropyl)-5-hydroxy-1,3-benzenedicarboxamide (II) is achieved.

Compound (I) is obtained along with the corresponding mono- and di-iodinated intermediates and iodide ions (I$^-$) are released from the reaction. Preferably, the molar ratio of $I_2$ to N,N'-(2,3-dihydroxypropyl)-5-hydroxy-1,3-benzenedicarboxamide (II) is in the range from 2:1 to 1.5:1, preferably 1.5:1.

During step b"$_1$, only half of the iodine atoms provided can react with the substrate, since the high concentration of H+ ions discourages a further removal of protons from compound (II), thus blocking the electrophilic substitution. Therefore, after this chemical step, the reaction mixture comprises not only a percentage of compound (I) but also a residual amount of unreacted compound (II) as well as the corresponding mono- or di-iodinated intermediates.

The reaction is preferably carried out at a temperature ranging from 50° C. to 70° C., more conveniently of about 60° C., and for a time ranging from 5 min to 20 min, typically about 10 minutes.

Optionally, the steps a" and b"$_1$, carried out without electrochemical support, can be performed in a separate container and then transferred in an electrochemical cell when performing step b"$_2$, even though it can be more convenient to keep the solution in the same cell from the beginning.

Step b"$_2$) is carried out by applying a constant electric potential (potentiostatic mode), to the magnetically stirred solution obtained from step b"$_1$). In this way, the iodide ions obtained in step b"$_1$) after the iodination reaction are re-oxidized to molecular iodine ($I_2$) which reacts with the remaining N,N'-(2,3-dihydroxypropyl)-5-hydroxy-1,3-benzenedicarboxamide (II) or with the corresponding mono- and di-iodinated intermediates present in the reaction mixture to complete the tri-iodination of compound (II).

The solution is maintained at a temperature ranging from 50° C. to 70° C., preferably 60° C.

Preferably, the reaction is carried out with an anode potential comprised between 0.6 V and 0.8 V vs. SCE, more preferably between 0.65 V and 0.7 V vs SCE.

The reaction medium is maintained at a basic pH, i.e. about 8-12, by addition of a strong base, such as NaOH pellets, which buffers the acidity progressively developed. The pH must be controlled in particular when the reaction is carried out in a two compartments cell with a cationic membrane.

The amount of base needed for the neutralization of the electrochemical reaction can be added in a single transfer or gradually, before or during step b"$_2$. Preferably, a stoichiometric amount of NaOH is added before carrying out the electrochemical step b"$_2$.

The stoichiometry of the reactions involved in this process are reported below:

Compound (I) iodination: $6I_2+2$Compound (II)$\rightarrow 2$Compound (I)$+6H^++6I^-$ Cathodic process: $6H^++6e^-\rightarrow 3H_2$ Anodic reaction: $6I^-\rightarrow 3I_2+6e^-$ Overall reaction: $3I_2+2$Compound (II)$\rightarrow 2$Compound (I)$+3H_2$ The reaction of iodination of N,N'-(2,3-dihydroxypropyl)-5-hydroxy-1,3-benzenedicarboxamide (II) produces three iodide ions and three protons for each product molecule.

Advantageously, the electrochemical reaction of step b"$_2$) allows to re-oxidize at the anode the produced iodide ions (which would be lost during the work-up of the reaction, generating a loss of 50% of the precious halogen atoms) and to reintroduce them into the process until they are completely used and/or until the compound (II) is completely converted to compound (I) by converting them directly in situ into the iodinating agent $I_2$. Protons (H$^+$), also generated in this process, are reduced to gaseous hydrogen (H$_2$) onto the cathode surface. Optionally, in all embodiments the gaseous hydrogen thus produced can then be recovered by methods conventionally used in electrochemical industrial processes, for instance by means of recovery membranes and the like.

Figure 4A:
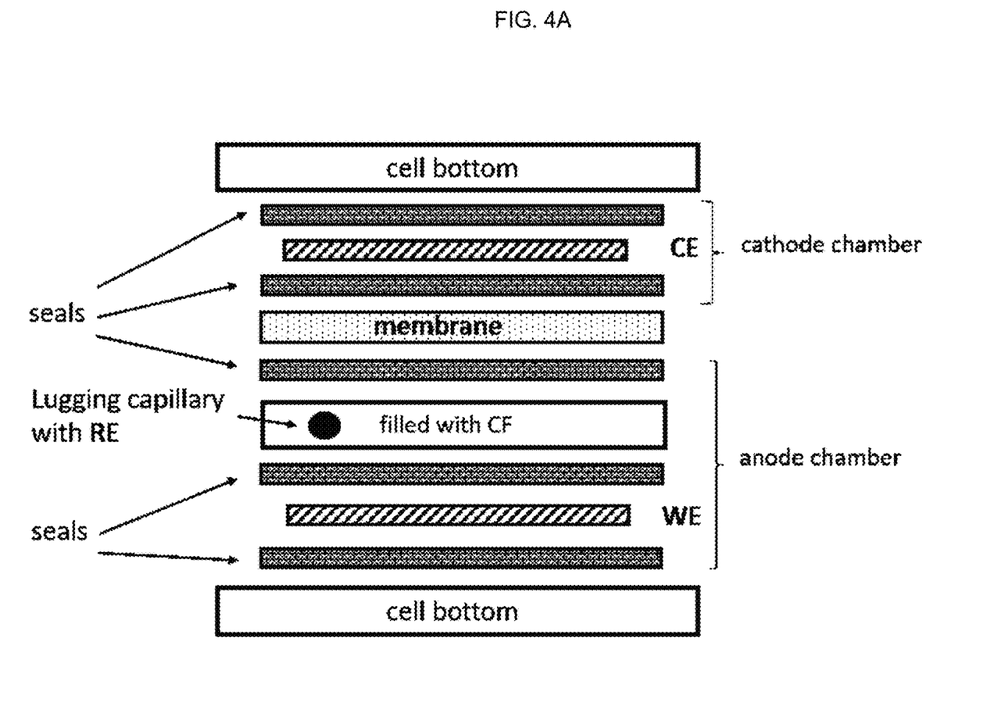
FIG. 4 represents a representative example of flow electrochemical cell, alone (a) and integrated in the flow system (b) where the anolyte and catholyte solutions are recirculated according to one embodiment of the invention.
Figure 4B:
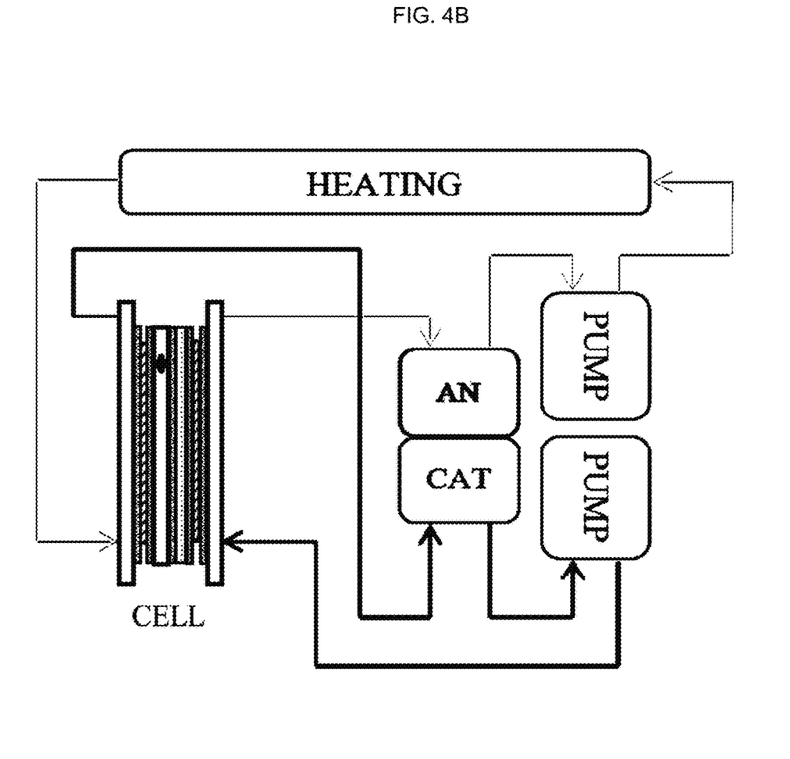

Preferably, the electrochemical reaction of step b"$_2$, performed in potentiostatic mode, can be also carried out in a two-compartments filter-press cell in flux conditions, wherein the electrolyte solutions are recirculated. FIG. 4 for instance shows a representative example of a flow system comprising a filter-press cell (a) and a circuit with two pumps (e.g. centrifugal or peristaltic pumps) for the recirculation of the solutions and heating means for keeping the temperature at 50-70° C. (b). For instance, according to the latter described embodiment, the electrolyte solutions are represented by the aqueous mixture of compound (II) and $I_2$ as defined in step a" (anolyte) and a 0.1 M NaOH solution (catholyte).

Surprisingly, when operating with a flow system the compound (I) was obtained with yields of about 100%. Such system thus demonstrates that the process of the invention can be potentially used on a large-scale plant and integrated in an industrial production of iomeprol or other iodinated contrast agents.

The process of invention, as exemplified in all the above embodiments, is therefore a very efficient process which allows to achieve the tri-iodination of N,N'-(2,3-dihydroxypropyl)-5-hydroxy-1,3-benzenedicarboxamide (II) in high yields and without loss of iodine. All the iodine atoms put in the cell in fact are exploited for the iodination reaction.

Subsequent work-up of the reaction mixture can be accomplished according to conventional methods known in the art in order to isolate the final compound of formula (I).

It is another object of the invention the process as above defined further comprising a step c) of isolating the compound of formula (I) obtained through the electrochemical iodination of compound (II) according to the process described above.

The intermediate of formula (II) is a known starting material which can be prepared according to known methods. For a general reference, see for instance the aforementioned WO00/32561.

The compound of formula (I) is a useful intermediate for the synthesis of X-ray contrast agents, in particular Iomeprol (N,N'-bis[2,3-dihydroxypropyl]-5(hydroxyacetyl)methylamino]-2,4,6-triiodo-1,3-benzenedicarboxamide), as described above.

Hence, it is a further object of the present invention the use of the intermediate compound of formula (I), obtained through the electrochemical iodination of compound (II) as per steps a) and b) of the process of the invention, in the preparation of N,N'-bis[2,3-dihydroxypropyl]-5(hydroxyacetyl)methylamino]-2,4,6-triiodo-1,3-benzenedicarboxamide (IV, Iomeprol).

Preferably, object of the invention is a process for preparing N,N'-bis[2,3-dihydroxypropyl]-5(hydroxyacetyl)methylamino]-2,4,6-triiodo-1,3-benzenedicarboxamide (IV) comprising the steps of:
a) dissolving N,N'-(2,3-dihydroxypropyl)-5-hydroxy-1,3-benzenedicarboxamide (II) in a reaction medium in the presence of molecular iodine ($I_2$);
b) iodinating said compound (II) with molecular iodine ($I_2$) to obtain said compound (I);
c) isolating said compound (I);
d) reacting compound (I) with $ClCH_2(CO)NHCH_3$ to obtain the intermediate (III)

(III)

e) subjecting said intermediate (III) to Smile's rearrangement in the presence of a base, so as to obtain the final compound N,N'-bis[2,3-dihydroxypropyl]-5(hydroxyacetyl)methylamino]-2,4,6-triiodo-1,3-benzenedicarboxamide (IV)

(IV)

wherein the reaction medium of step a) is an aqueous solution, and the molecular iodine ($I_2$) in step b) is in situ electrochemically generated from a source of iodide ions ($I^-$).

Preferably, the reaction medium of step a) is water.

For a general reference to the conditions of the above steps d) and e) see WO00/32561.

The compound of formula (II) as starting material of the present process is known and may be prepared according to known methods, as reported above. Likewise, any other reactant and/or solvent being employed in the present process is known and readily available.

With the aim to better illustrate the present invention, without posing any limitation to it, the following examples are given with details concerning the different embodiments of the invention.

Experimental Section

For the examples reported below, the following experimental conditions were used:
multiple-necked, round bottomed flasks have been used as undivided electrochemical cells, by fitting the electrodes in the available necks (two electrode system). A power Supply Lafayette ALP-5A provided the constant current required to run the electrochemical steps. A platinum foil (0.1 mm thick) was used as the anode. A graphite rod was used as the cathode, except for pulsating or alternating current experiments where a platinum foil was used. The electrolysis was carried out in galvanostatic mode; or two-compartments cell comprising three electrodes: a working electrode (WE, carbon based anode), a counter electrode (CE, made of stainless steel) and a reference electrode (RE, represented by a saturated calomel electrode (SCE)). The two compartments were separated by cationic membrane (e.g. Nafion) and the SCE was accommodated in a Luggin capillary (polyethylene tube, 2 mm diameter), in contact with the anolyte of the anodic compartment. Depending on the experiments, the system was equipped with one or more of the following: a pHmeter, a thermostat, a potentiostat and hydraulic pumps. The electrolysis was carried out in potentiostatic mode, setting a chronoamperometry at constant potential.

Example 1

Electrochemical Iodination in Galvanostatic Mode Starting from Iodide Ions (NaI)

A 23.5% w/w aqueous solution of N,N'-(2,3-dihydroxypropyl)-5-hydroxy-1,3-benzenedicarboxamide (II) (0.34 mmol) was placed into an undivided electrochemical cell equipped with a graphite cathode and a platinum anode with NaI (1.34 mmol) and water (50 mL). The electrolysis was conducted in galvanostatic mode, i.e. the amount of current through the cell was kept constant with $\delta=8$ mA/cm². The solution was stirred at 50° C. and the pH was kept constant at 7 by continuous addition of 98% $H_2SO_4$. On the cathode surface an evolution of hydrogen was noticeable. Iodine was immediately formed on the anode surface and slowly dissolved by reaction with N,N'-(2,3-dihydroxypropyl)-5-hydroxy-1,3-benzenedicarboxamide (II). The current was periodically switched off to allow the complete dissolution of the iodine deposited onto the anode. After 3 h of reaction, the HPLC analysis showed the presence of mono and di-iodinated intermediates. After 48 h of reaction, the HPLC showed a 90% content (HPLC peak area %) of the tri-iodinated compound of formula (I).

Example 2

Electrochemical Iodination in Galvanostatic Mode Starting from 12

A 23.5% w/w aqueous solution of N,N'-(2,3-dihydroxypropyl)-5-hydroxy-1,3-benzenedicarboxamide (II) (0.34 mmol) was placed into an undivided electrochemical cell equipped with a graphite cathode and a platinum anode with molecular iodine (9.8 mmol) and water (7 mL). The mixture was magnetically stirred at 55° C. After 2 h, the HPLC analysis (peak area %) showed a 54% content of the tri-iodinated compound of formula (I) along with the presence of the corresponding mono- and di-iodinated intermediates. At this point the current was switched on and the electrolysis was conducted in galvanostatic mode with $5=8$ mA/cm². The solution was stirred at 55° C. and the pH was kept constant at 7 by continuous addition of 98% $H_2SO_4$. On the cathode surface an evolution of hydrogen was noticeable while on the anode surface the formation of iodine was evident. After 48 h the HPLC analysis (HPLC peak area %) showed a 90% content of N,N'-bis-(2,3-dihydroxypropyl)-5-hydroxy-2,4,6-triiodo-1,3-benzenedicarboxamide (I).

Example 3

Electrochemical Iodination in Potentiostatic Mode (Two-Compartments Cell) Starting from 12

A 23.3% w/w aqueous solution of N,N'-(2,3-dihydroxypropyl)-5-hydroxy-1,3-benzenedicarboxamide (II) (72 mmol, 100 mL) and $I_2$ (29.46 g) were placed into an electrochemical cell with two compartments divided by a cationic membrane (Nafion), equipped with an electrode made of stainless steel, nickel or platinum foil (cathode), a graphite rod (anode) and a saturated calomel electrode as reference (SCE). The catholyte was aqueous 0.5 M NaOH.

The mixture was magnetically stirred at about 65° C. and the pH kept between 10 and 12 by continuous addition of NaOH pellets. After 10 minutes the solution was yellow-orange and the HPLC analysis showed a 55% content of N,N'-bis-(2,3-dihydroxypropyl)-5-hydroxy-2,4,6-triiodo-1,3-benzenedicarboxamide (I), along with the presence of the corresponding mono- and diiodinated intermediates. At this point NaOH (113 mmol) was added progressively, still keeping the temperature at 65° C. and the pH at 10-12, and the electrolysis was carried out in potentiostatic mode by setting a chronoamperometry at the constant potential of 0.7 V vs SCE After 35 hours of reaction, the HPLC analysis showed a 90% content (HPLC peak area %) of N,N'-bis-(2,3-dihydroxypropyl)-5-hydroxy-2,4,6-triiodo-1,3-benzenedicarboxamide (I).

Example 4

Electrochemical Iodination Scale-Up in Potentiostatic Mode (Flow Electrochemical Cell)

A 23.3% w/w aqueous solution of N,N'-(2,3-dihydroxypropyl)-5-hydroxy-1,3-benzenedicarboxamide (II) (576 mmol, 800 mL) and $I_2$ (220.4 g) were slowly placed into a 1 L glass bottle. The solution was maintained under stirring and heated at about 55-60° C. until the color of the solution changed from dark red to a clear yellow-orange, with the pH stable at about 10.

After 10 minutes, the HPLC analysis showed a 55% content of N,N'-bis-(2,3-dihydroxypropyl)-5-hydroxy-2,4,6-triiodo-1,3-benzenedicarboxamide (I), along with the presence of the corresponding mono- and di-iodinated intermediates.

At this point the solution was transferred into the anolyte chamber of a filter-press electrochemical cell for flow electrolysis, as illustrated in FIG. 4. Such cell, having dimensions of 10×30 cm, was made of two compartments divided by a cationic membrane (Nafion® 117) and equipped with a stainless-steel mesh cathode (CE), a carbon cloth strip with a platinum foil as anode (WE) and a saturated calomel electrode as reference (SCE) accommodated into a Luggin capillary (polyethylene, 2 mm diameter). The anodic compartment (about 180 cm³) was completely filled with 5 layers of carbon felt (AvCarb® Style G300A) and the catholyte compartment was filled with 1 L of 0.1 M NaOH. The carbon cloth anode is connected to the external electric circuit by means of a metallic (e.g. Pt) foil. Both the solutions of compound (II)+$I_2$ in the anodic compartment and 0.1 M NaOH in the cathodic compartment were recirculated by using two membrane pumps at 0.3 L/min.

The anolyte temperature was kept at about 65° C. by heat exchanging with hot water and the electrolysis was conducted in potentiostatic mode by setting a chronoamperometry at the constant potential of 0.65 V vs SCE. About 35 g of NaOH pellets were continuously added in order to keep the pH between 10 and 12.

After 9.3 hours of reaction, the color of the anolyte was orange and the HPLC analysis showed a 100% content (HPLC peak area %) of N,N'-bis-(2,3-dihydroxypropyl)-5-hydroxy-2,4,6-triiodo-1,3-benzenedicarboxamide (I).

Due to the strong basic pH of the mixture, as the consequence of NaOH addition during the reaction, the product was isolated and characterized in the form of the corresponding sodium phenate.

$^1$H- and $^{13}$C-NMR analyses confirmed the absence of any side-product, such as hydrolysis products.

Spectral data: $^1$H-NMR (400 MHz, DMSO-d6, 363K):

| | |
|---|---|
| 7.34 ppm | broad s [2H], 2 × NH |
| 4.32 ppm | broad s [2H], 2 × OH |
| 4.15 ppm | broad s [2H], 2 × OH |
| 3.73 ppm | app. q, J = 5.6 Hz (average), [2H], 2 × CH—OH |
| 3.51 ppm | dd, $J_a$ = 11.1 Hz, $J_b$ = 5.1 Hz [2H], 2 × $H_a$ CH$_2$—OH |
| 3.46 ppm | dd, $J_a$ = 11.1 Hz, $J_b$ = 5.6 Hz [2H], 2 × $H_b$ CH$_2$—OH |
| 3.33 ppm | dd, $J_a$ = 13.2 Hz, $J_b$ = 6.0 Hz [2H], 2 × $H_a$ CH$_2$—NH |
| 3.16 ppm | dd, $J_a$ = 13.2 Hz, $J_b$ = 5.7 Hz [2H], 2 × $H_b$ CH$_2$—NH |

$^{13}$C NMR (100 MHz, DMSO-d$_6$, 300K):

| | |
|---|---|
| 170.73 ppm | 2 × CONH |
| 164.89 ppm | C5 |
| 147.29 ppm | C1 and C3 |
| 87.79 ppm | C2 and C4 |
| 70.20 ppm | 2 × CH—OH |
| 63.98 ppm | 2 × CH$_2$—OH |
| 57.91 ppm | C6 |
| 42.64 ppm | 2 × CH$_2$—NH |

REFERENCES

1. Gallotti et al., Eur. J. Radiol., 1994, 18(S1), S1-S2;
2. WO00/32561;
3. WO2011/003894
4. WO2011/154500;
5. WO2009/103666.

The invention claimed is:

1. A process for the preparation of N,N'-bis-(2,3-dihydroxypropyl)-5-hydroxy-2,4,6-triiodo-1,3-benzenedicarboxamide (I), comprising the steps of:
   a) dissolving N,N'-(2,3-dihydroxypropyl)-5-hydroxy-1,3-benzenedicarboxamide (II) in a reaction medium in the presence of molecular iodine (I$_2$) and
   b) iodinating said compound (II) with the molecular iodine (I$_2$) to obtain said compound (I), wherein the reaction medium is an aqueous solution and the molecular iodine (I$_2$) is in situ electrochemically generated from a source of iodide ions (I$^-$) and wherein steps a) and b) are carried out in galvanostatic mode using an undivided electrolytic cell or in potentiostatic mode using an electrolytic cell formed by two-compartments divided by a porous septum or by a ionic exchange membrane.

2. The process according to claim 1 wherein the aqueous solution is water.

3. The process according to claim 1, wherein the molecular iodine (I$_2$) is electrochemically generated from the source of iodide ions (I$^-$) by applying a constant electric current, and wherein the source of iodide ions (I$^-$) is selected from HI and an alkali metal iodide.

4. The process according to claim 3, wherein the applied electric current is comprised in the range from 5 to 100 mA/cm$^2$.

5. The process according to claim 3, wherein the alkali metal iodide is NaI or KI.

6. The process according to claim 1, wherein in galvanostatic mode said molecular iodine (I$_2$) is electrochemically re-generated from iodide ions (I$^-$) produced by the reaction of N,N'-(2,3-dihydroxypropyl)-5-hydroxy-1,3-benzenedicarboxamide (II) with I$_2$ by applying a constant electric current which is switched on after a time ranging from 1 hour to 6 hours.

7. The process according to claim 6, wherein the reaction medium is kept at a pH comprised in the range from 5 to 7.5 by addition of a protic acid and at a temperature comprised between 40°° C. and 60° C.

8. The process according to claim 1, wherein in potentiostatic mode said molecular iodine (I$_2$) is electrochemically re-generated from iodide ions (I$^-$) produced by the reaction of N,N'-(2,3-dihydroxypropyl)-5-hydroxy-1,3-benzenedicarboxamide (II) with I$_2$ by applying a constant voltage producing an anode potential from 0.5 to 0.9 V vs SCE (saturated calomel electrode).

9. The process according to claim 8, wherein the reaction medium is kept at a pH from 10 to 12 by addition of a strong base and at a temperature comprised between 50° C. and 70° C.

10. The process according to claim 1, wherein the two compartments of the cell are separated by said ionic exchange membrane selected from a cationic membrane.

11. The process according to claim 1, wherein the two-compartments electrolytic cell comprises an anodic compartment filled with an aqueous solution of compound (II) and I$_2$ according to step a) of claim 1 (anolyte) and a cathodic compartment filled with a 0.1-0.5 M NaOH solution (catholyte).

12. The process according to claim 11 which is carried out in flux conditions by recirculating the aqueous solution of compound (II) and I$_2$ (anolyte) and the 0.1-0.5 M NaOH solution (catholyte).

13. The process according to claim 1 further comprising the following step:
   c) isolating the N,N'-bis-(2,3-dihydroxypropyl)-5-hydroxy-2 4,6-triiodo-1,3-benzenedicarboxamide (I) obtained through the electrochemical iodination of N,N'-(2,3-dihydroxypropyl)-5-hydroxy-1,3-benzenedicarboxamide (II).

14. The process according to claim 1, wherein said molecular iodine (I$_2$) is electrochemically re-generated from iodide ions (I$^-$) produced by the reaction of N,N'-(2,3-dihydroxypropyl)-5-hydroxy-1,3-benzenedicarboxamide
(II) with I$_2$ by applying a constant voltage producing an anode potential from 0.65 to 0.7 V vs SCE (saturated calomel electrode).

15. A process for preparing N,N'-bis-[2,3-dihydroxypropyl]-5-(hydroxyacetyl) methylamino]-2,4,6-triiodo-1,3-benzenedicarboxamide (IV) comprising the steps of:
   a) dissolving N,N'-(2,3-dihydroxypropyl)-5-hydroxy-1,3-benzenedicarboxamide (II) in a reaction medium in the presence of molecular iodine (I$_2$);
   b) iodinating said compound (II) with the molecular iodine (I$_2$) to obtain N,N'-bis-(2,3-dihydroxypropyl)-5-hydroxy-2,4,6-triiodo-1,3-benzenedicarboxamide (I);
   c) isolating said compound (I);
   d) reacting said compound (I) with ClCH2 (CO) NHCH3 to obtain the intermediate (III)

(III)

e) subjecting said intermediate (III) to Smile's rearrangement in the presence of a base, so as to obtain N,N'-bis[2,3-dihydroxypropyl]-5-(hydroxyacetyl) methylamino]-2,4,6-triiodo-1,3-benzenedicarboxamide (IV)

(IV)

wherein the reaction medium of step a) is an aqueous solution, and the molecular iodine ($I_2$) in step b) is in situ electrochemically generated from a source of iodide ions ($I^-$) and wherein steps a) and b) are carried out in
galvanostatic mode using an undivided electrolytic cell or in potentiostatic mode using an electrolytic cell formed by two-compartments divided by a porous septum or by a ionic exchange membrane.

* * * * *